United States Patent
Lee

Patent Number: 6,052,183
Date of Patent: Apr. 18, 2000

[54] IN-SITU PARTICLE MONITORING

[75] Inventor: Szetsen Steven Lee, Hsinchu, Taiwan

[73] Assignee: Winbond Electronics Corp, Hsinchu, Taiwan

[21] Appl. No.: 09/292,771

[22] Filed: Apr. 14, 1999

[51] Int. Cl.$^7$ .................................................. G01N 21/00
[52] U.S. Cl. ......................... 356/337; 356/338; 356/343
[58] Field of Search ................................... 356/337, 338, 356/343

[56] References Cited

U.S. PATENT DOCUMENTS 5,255,089  10/1993  Dybus et al. ........................... 356/337

*Primary Examiner*—Frank G. Font
*Assistant Examiner*—Reginald A. Ratliff
*Attorney, Agent, or Firm*—W. Wayne Liauh

[57] ABSTRACT

A method for monitoring the presence of particles in a plasma etch chamber. It includes the steps of: (a) selecting at least one laser light source whose wavelength is at such an energy which will cause the particles to be monitored inside the plasma etch chamber to emit Raman, Stoke, and anti-Stoke spectra lines when the laser light is scattered by the particle; (b) emitting the laser light into an internal space of the plasma etch chamber; and (c) using a set of fiber optics to intercept light that may be scattered by the particle, if the particle is present in the plasma etch chamber; and (d) measuring amplitude and spectra of the scattered light. Because the intensity of the scattered light is proportional to the dielectric constant to the fourth power, the method is most advantageous for detect the presence of metal-containing particles, which have a very high dielectric constant. The spectral analysis also provides information relating to the chemical composition of the particles.

10 Claims, 2 Drawing Sheets

IN-SITU PARTICLE MONITORING

FIELD OF THE INVENTION

The present invention relates to an improved plasma etching chamber with an in-situ particles monitoring capability and the process of utilizing the same, for the manufacturing of semiconductor devices. More specifically, the present invention relates to a non-intrusive method for the in-situ monitoring of the number density and size of particles that may be formed and accumulate in the plasma etching chamber during the fabrication of semiconductor devices. The method and apparatus disclosed in the present invention are most advantageous for monitoring the presence of metal-containing particles in the etching chamber. Another advantage of the novel method and apparatus disclosed in the present invention is that it can be fine-tuned to monitor the chemical composition of the particles, including non-metal particles.

BACKGROUND OF THE INVENTION

Plasma etching is one of the most commonly employed techniques in the fabrication of semiconductor devices. It involves the selective removal of material by reactive free radicals or ions generated with a plasma. As it is well known in the art, plasma is an ionized gas in which concentrations of positive and negative ions are almost equal. The plasma may also contain free radicals which are electrically neutral yet highly reactive. Typically, a plasma is formed by introducing a predetermined gas into a plasma chamber and applying a radio frequency (RF) field to the plasma chamber. The gas introduced is chosen such that it will participate in the intended chemical reaction of a particular process. The RF field causes electron collisions with neutral or charged species to emit radiation. During the etching of semiconductor layer materials, halogen-containing compounds are commonly used in the gas phase as an etching gas to remove silicon based dielectric material.

One of the problems associated with the plasma etching process is the formation of particles which can cause defects due to particles fallen on the wafer surface. U.S. Pat. No. 5,362,356 discloses a passive, in-line method of monitoring film removal during plasma etching based on interference phenomena. In the method disclosed in the '356 patent, plasma emission intensity is monitored at a selected wavelength and variations in plasma emission intensity are correlated to the remaining film thickness, etch rate and uniformity, and etch selectivity. The method is most useful in conjunction with nitride island etch, polysilicon etch, oxide spacer etch, contact etch, etc; it can also be used in determining a particular remaining film thickness (e.g., just prior to clearing) at which point the etch recipe can be changed from a high-rate, low selectivity etch to a low-rate, high-selectivity etch.

U.S. Pat. No. 5,467,188 discloses a particle detecting system for detecting the number and size of particles generated in a process chamber of a semiconductor manufacturing system. The particle detecting system disclosed in the '188 patent includes a small detection chamber and a particle detector. The small detection chamber has an internal space thereof provided outside a wall portion forming the process vacuum chamber, and a plurality of laser beam transmitting windows and scattered light extracting windows. The particle detector is arranged in an atmospheric environment outside the detection chamber and including a laser diode for emitting a laser beam into the detection chamber through the laser beam transmitting windows and photosensors for detecting scattered light generated within the detection chamber through the scattered light extracting windows. One of the key element of the detection chamber of the '188 patent is that the structure is detachably attached to the process chamber. The particle detector is formed as a module, and can be attached to the detection chamber from outside the detection chamber. The particle detector has such a structure as to be detachably attached to the detection chamber.

U.S. Pat. No. 5,632,855 discloses a process for etching thermally grown oxide. The process involves a plurality of pre-stabilizing steps, followed by an etch step, which is then followed by a plurality of post-stabilizing steps. The post-stabilizing steps include a particle removal or byproduct flush step in addition to the post-stabilizing steps. The process parameters are chosen to remove thermal oxide within contact regions at a uniform rate. The resulting thermal oxide is substantially uniform with less than 3.0% variance in thickness across the contact regions and across like areas of the entire wafer surface. Bu utilizing the post-stabilize steps and the process parameters chosen for each step thereby provides an improved etch uniformity of thermal oxide films within fine-line areas.

U.S. Pat. No. 5,854,138 discloses a method for fabricating semiconductor and/or integrated circuit having reduced particulate count upon or within the circuit in which particles which formed within the plasma used to effectuate etch or deposition are gradually swept from the region above the integrated circuit, during power ramp down post etch or deposition. Plasma, and more specifically, the field which forms the plasma is maintained but at reduced levels to allow gradual reduction of particles through a multitude of steps. The steps culminate in eliminating power to the electrodes and plasma between the electrodes. However, at the time at which power is absent, only a few of the original particles remain in the critical region above the integrated circuit. Residual particles are removed in a purge step following the successive sequence of ramp down steps. Gap between the electrodes is increased to a final position early in the ramp down sequence so that additional electrode movement does not occur when the field is weakened.

The above prior art references illustrate the importance of controlling the particles formation during the semiconductor fabrication processes. However, no satisfactory solution has been offered to monitor the number density and size of the particles that may be formed during the plasma etching process. Light scattering technique has been well known in the art as a useful tool for measuring the number density and size of particles. However, light scattering technique has not been considered a viable approach for use in the plasma etching chamber, mainly because of the relatively low particle density and the high noise level, as a result of the constant changes in the component compositions and other dynamic nature in the plasma etching chamber, rendering the measured results highly unreliable.

The method disclosed in the '188 patent involves the addition of a small detecting chamber external to the main etching chamber. This may improve the sensitivity of the light scattering measurement, but it may also cause a disruption in the plasma flow pattern inside the etching chamber, and thus, may not be desired. U.S. Pat. Nos. 4,804,853, 4,739,177, 5,132,548 proposed the use of light scattering techniques in semiconductor fabrication processes. However, these techniques would suffer the same problems as discussed above if used in an etching chamber. Indeed, the '188 patent specifically mentioned that the techniques disclosed in these patents would adversely affect the quality of the semiconductor products.

SUMMARY OF THE INVENTION

The primary object of the present invention is to develop a novel plasma etching method with improved in-situ monitoring capability, and an improved plasma etching chamber incorporating this novel process, for the fabrication of semiconductor devices. More specifically, the primary object of the present invention is to develop an improved and in-situ technique which utilizes a light scattering technique to continuously monitor the presence of particles that may be formed inside a plasma etch chamber, so as to ensure good quality of semiconductor devices fabricated inside the plasma etch chamber. Preferably, the method so developed is non-intrusive, including that it will not affect the plasma flow inside the etching chamber.

Because of a number of unfavorable factors, light scattering technique has not been considered as a practical approach for obtaining useful information of particles that may be formed inside an etching chamber. The basic theory that describes the scattered light intensity can be summarized according to the following equation:

$$\frac{I_{scatter}}{I_o} = \frac{8\pi^3 k_B T \kappa (\varepsilon - 1)^2 (\varepsilon + 2)^2 V}{27\lambda^4} \quad \text{(Eqn. 1)}$$

where: $I_{scatter}$ is the scattered light intensity, $\lambda$ is the wavelength of the light source, $\varepsilon$ is the dielectric constant of the particle scattering light, $\kappa$ is the isothermal compressibility $\left( = -\frac{1}{V}\frac{\partial V}{\partial P} \right)$, and $V$ is the total volume of the scattering body, i.e., the particles.

As it can be seen in Equation 1, because etching is typically conducted in a highly vacuum environment, the number density (i.e., the total volume of the scattering body, V) is typically very small, and the scattered light intensity that can be expected will also be very small. Thus, the light scattering measurement may not give very reliable results, as the measured scattered light intensity is expected to be buried under the noise level and the baseline shifting typically avoidable in any measurement, especially when the measurement is conducted in a dynamic environment such as an etching chamber. The light scattering data also do not provide information regarding the composition of the scattering body.

However, the inventor of the present invention has unexpectedly discovered that, in light of the obvious problems as discussed above, light scattering technique can actually be effectively utilized to provide in-situ monitoring of metal particles. Based on this observation, an improved etching chamber can be constructed which provides the capability for the in-situ monitoring of at least metal particles. The improved etching chamber of the present invention can also be utilized to monitor the presence of non-metal particles, such as fluorocarbon polymer flakes, which also exhibit a relatively high dielectric constant. By other adjustments, the present invention can also be utilized to provide the chemical composition of the particle or particles being monitored.

One characteristic of metal particles is that they have very high values of dielectric constant, often in the range exceeding 10,000. At such a large value, Equation 1, the light scattering equation, can be reduced to the follow equation:

$$\frac{I_{scatter}}{I_o} = \frac{8\pi^3 k_B T \kappa \varepsilon^4 V}{27\lambda^4} \quad \text{(Eqn. 2)}$$

Equation 2 shows that, for metal particles with a very high dielectric constant, the scattered light intensity is proportional to the fourth power of the dielectric constant (i.e., $\varepsilon^4$). Therefore, when there is a trace of metal-containing particles in the etching chamber, a strong signal can be detected by the in-situ light-scattering-based monitor. This observation makes the in-situ monitoring process of the present invention particularly useful for detecting the presence of metal-containing particles.

Another important feature of the improved etching chamber of the present invention is that it also measures the spectrum of the scattered light. By properly choosing the wavelength of the laser light source, the light scattering spectrum will also provide the information relating to the chemical composition of the scattering particle.

It is known that, when a particle is bombarded with a light beam, if there are certain energy levels characteristic of the atoms contained in the particle which can resonate with the energy of incident light (i.e., "$1/\lambda$"), then there are three possible levels at which the outgoing (i.e., scattered) light will carry its energy. These three energy levels include: (1) same energy as the incident light (Raman scattering), (2) lower energy level than the incident light (Stoke scattering), and (3) higher energy level than the incident light (Anti-Stoke scattering). Different particles with different chemical compositions (such as metal, polymer, oil, oxide, etc.) will have different Stoke and anti-Stoke spectra, in addition to the common Raman spectrum. The distribution of the scattered spectral lines can be advantageously utilized to give an indication of the chemical composition of the particles being monitored. And this is another important feature of the etching chamber disclosed in the present invention. By properly selecting the laser light source, the operator can also monitor the presence of non-metal particles.

BRIEF DESCRIPTION OF THE DRAWING

The present invention will be described in detail with reference to the drawing showing the preferred embodiment of the present invention, wherein.

DETAILED DESCRIPTION OF THE PREFERRED EMBODIMENT

The present invention discloses an improved plasma etching chamber and method which utilize a non-intrusive in-situ light scattering assembly to continuously monitor the presence of particles that may be formed inside a plasma etch chamber, as well as the chemical composition of the particles so formed, so as to ensure good quality of semiconductor devices fabricated inside the plasma etch chamber.

Figure 2:
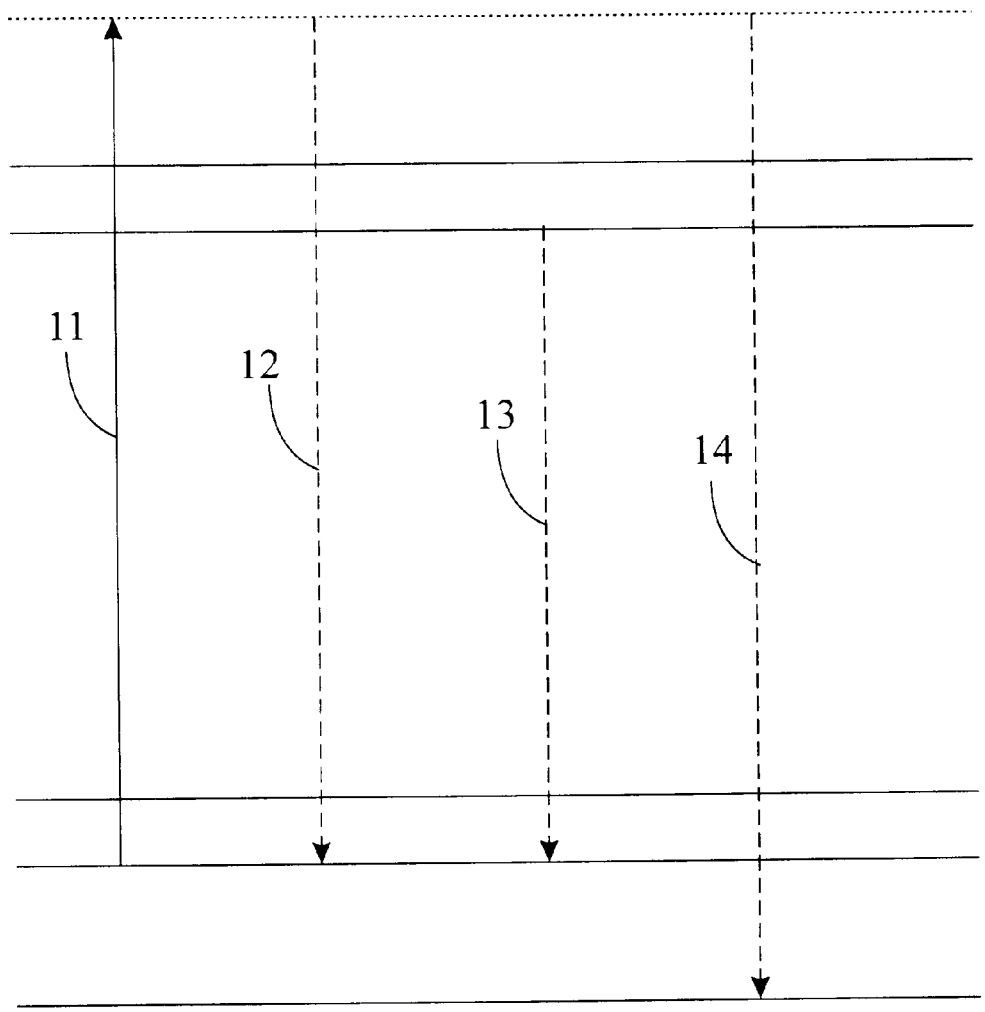
FIG. 2 is a plot showing the three possible levels of the scattered light when the incident light is properly selected such that the constituting atoms of a particle to be monitored contains at least one energy level that can resonate with the energy level of the incident light.

One of the key elements of the present invention is to select the light source whose energy level (which is inversely proportional to the wavelength of the light source) is such that it can cause the atoms contained in the target particles to resonate. FIG. 2 is a plot showing the three possible levels of the scattered light when the laser light source 11 is properly selected such that the constituting atoms of the type of particles to be monitored contain at least one energy level that can resonate with the energy level of the selected incident light. These three energy levels include: (1) same energy as the incident light (Raman scattering 12), (2) lower energy level than the incident light (Stoke scattering 13), and (3) higher energy level than the incident light (Anti-Stoke scattering 14). Different particles with different chemical compositions (such as metal, polymer, oil, oxide, etc.) will have different Stoke and anti-Stoke spectra, in addition to the common Raman spectrum. By using a laser light with a predetermined wavelength and by analyzing the scattered light spectra, the method disclosed in the present invention can provide information relating to the chemical composition of the particles that scattered light. Furthermore, by using a plurality of laser light sources of varying wavelengths, different types of particles can be monitored, on an at least semi-qualitative basis.

The light-scattering-based in-situ monitoring assembly of the present invention is most advantageous for monitoring the presence of metal-containing particles. As it was discussed earlier, light scattering technique has not been considered as a practical means for providing information regarding particles that may be formed inside an etching chamber, and many prior art efforts proposed to utilize the light scattering technique have not been considered for use in etching chambers. This is believed to be attributed to the relatively low number density of the particles and the dynamic environment inside an etching chamber. The basic theory that describes the scattered light intensity can be summarized according to the following equation:

$$\frac{I_{scatter}}{I_o} = \frac{8\pi^3 k_B T \kappa (\varepsilon - 1)^2 (\varepsilon + 2)^2 V}{27 \lambda^4} \quad \text{(Eqn. 1)}$$

where: $I_{scatter}$ is the scattered light intensity, $\lambda$ is the wavelength of the light source, $\varepsilon$ is the dielectric constant of the particle scattering light, $\kappa$ is the isothermal compressibility $\left( = -\frac{1}{V}\frac{\partial V}{\partial P} \right)$, and $V$ is the total volume of the scattering body, i.e., the particles.

As discussed above, because etching is typically conducted in a high vacuum environment, the number density (i.e., the total volume of the scattering body, V) is typically very small. Thus, as it can be seen in Eqn. 1, the scattered light intensity that can be detected is often buried by the noise level and the baseline shifting often encountered in the measurement, especially when the measurement is conducted in a dynamic environment such as a plasma etching chamber, and the results from light scattering measurements may not be very reliable, resulting either an important warning signal being missed or false alarms being raised. This is not acceptable in a semiconductor fabricating process, which requires high reliability and high precision. The light scattering data also do not provide information that can be extracted to understand the composition of the scattering body.

However, when the light scattering assembly is focused on the monitoring of metal-containing particles, very different results are obtained. One characteristic of metal particles is that they have very high values of dielectric constant, often in the range in excess of 10,000. At such a large value, Equation 1, the light scattering equation, can be rewritten as follows:

$$\frac{I_{scatter}}{I_o} = \frac{8\pi^3 k_B T \kappa \varepsilon^4 V}{27 \lambda^4} \quad \text{(Eqn. 2)}$$

Equation 2 shows that, for metal particles with have a very high dielectric constant, the scatter light intensity is proportional to the fourth power of the dielectric constant. Therefore, when there is a trace of metal particles in the etching chamber, a strong signal can be detected by the in-situ monitor. This observation makes the in-situ monitoring process of the present invention particularly useful for detecting the presence of metal-containing particles.

Figure 1:
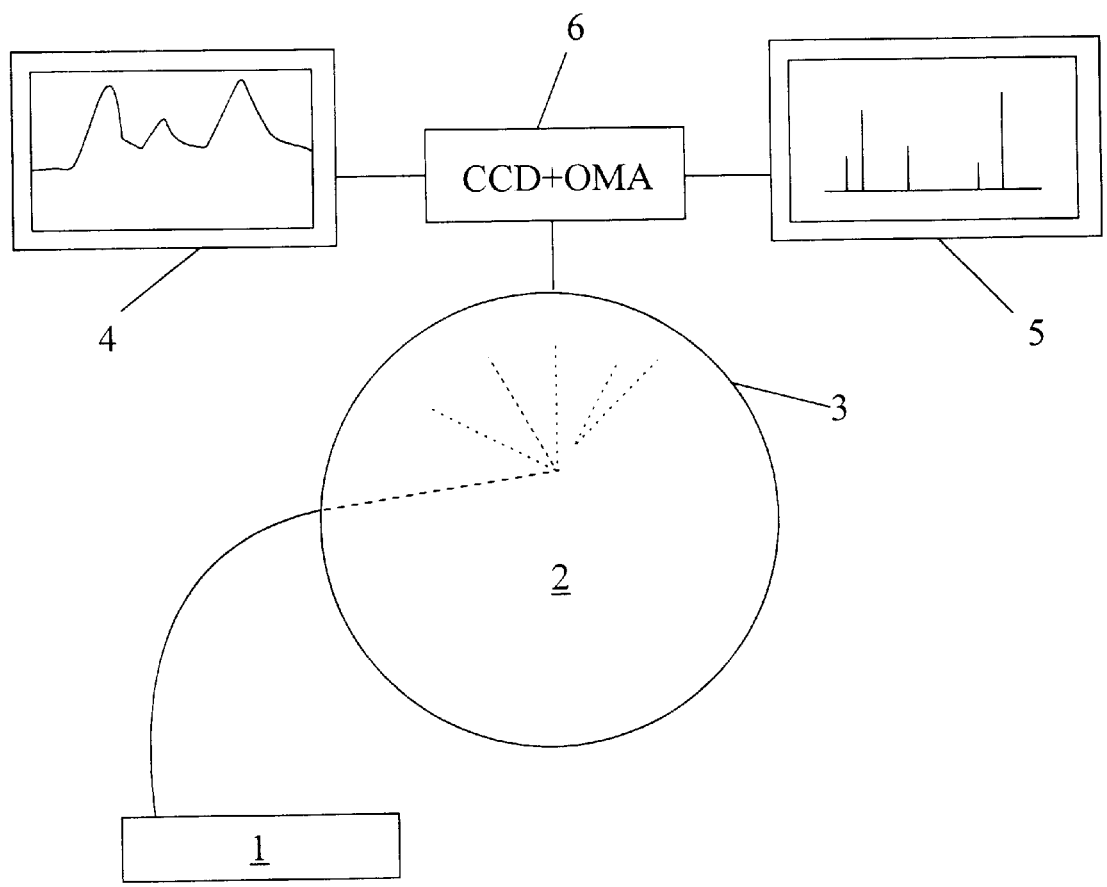
FIG. 1 is a schematic drawing of an improved plasma etching chamber according to a preferred embodiment of the present invention which includes a non-intrusive in-situ light scattering assembly for monitoring the presence of particles that may be formed inside the etching chamber.

FIG. 1 is a schematic drawing showing the improved plasma etching chamber according to a preferred embodiment of the present invention. The etching chamber 10 is provided with a laser light source 1 which emits light into the internal portion of the etching chamber. A fiber optic 2 is provided through the wall 3 of the etching chamber to capture the scattered light if there are particles present in the etching chamber 10. The scattered light so captured is transmitted through the fiber optic 2 to a CCD (charge-couple device) array which is connected to an OMA 6 (optical channel analyzer) to measure and display the amplitude (i.e., intensity) 4 and scattering spectra 5 of the captured scattered light. It should be noted that the novel design of the present invention allows the fiber optics to be used in the light scattering measurement, and no separate compartment is required. Thus, in the present invention, light is scattered within the etching chamber itself, and no interruption of the plasma flow is encountered.

FIG. 1 shows that a light intensity detector measures the intensity of the scattered light, and the spectrum analyzer provides the scattering spectra of the scattered light. As it has been discussed above, by properly choosing the wavelength of the laser light source, the light scattering spectra will also provide the information relating to the chemical composition of the scattering particle. More than one light laser light source can be utilized to expand the type of particles that can be monitored.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A method for monitoring an etching condition in a plasma etch chamber comprising the step of monitoring the presence of particles with high dielectric constants, said step further comprising the following sub-steps:

(a) selecting at least one laser light source whose wavelength is at such an energy which will cause a particle to be monitored inside a plasma etch chamber to emit Raman, Stoke, and anti-Stoke spectra lines when said laser light is scattered by said particle;

(b) emitting said laser light into an internal space of said plasma etch chamber; and (c) using a set of fiber optics to intercept light that may be scattered by said particle, if said particle is present in said plasma etch chamber; and (d) measuring amplitude and spectra of said scattered light.

2. The method for monitoring an etching condition in a plasma etch chamber according to claim 1, wherein said particles are metal-containing particles.

3. The method for monitoring an etching condition in a plasma etch chamber according to claim 1, wherein said set of fiber optics is formed through a wall of said plasma etch chamber.

4. The method for monitoring an etching condition in a plasma etch chamber according to claim 1 wherein said plasma etch chamber contains a plurality of said laser light sources each emitting a laser light with a unique wavelength so as to monitor a plurality of particles with different levels resonance energy.

5. The method for monitoring an etching condition in a plasma etch chamber according to claim 1 wherein said plasma etch chamber contains a charge-coupled-device array and an optical channel analyzer provided outside of said plasma etch chamber for instantaneous full spectral analysis and display.

6. A plasma etch chamber with an in-situ particle monitoring assembly, comprising:

(a) a plasma etch chamber;

(b) at least one laser light source which will emit laser light at a predetermined wavelength into an internal space of said plasma etch chamber, wherein said predetermined wavelength is selected such that said laser light will cause a particle to be monitored inside said plasma etch chamber to emit Raman, Stoke, and anti-Stoke spectra lines when said laser light is scattered by said particle;

(c) a set of fiber optics to intercept light that may be scattered by said particle, if said particle is present in said plasma etch chamber; and (d) light measuring device for measuring amplitude and spectra of said scattered light.

7. The plasma etch chamber according to claim 6, wherein said particles to be monitored are metal-containing particles.

8. The plasma etch chamber according to claim 6, wherein said set of fiber optics is formed through a wall of said plasma etch chamber.

9. The plasma etch chamber according to claim 6 which contains a plurality of said laser light sources each emitting a laser light with a unique wavelength so as to monitor a plurality of particles with different levels resonance energy.

10. The plasma etch chamber according to claim 6 which contains a charge-coupled-device array and an optical channel analyzer for instantaneous full spectral analysis and display.

* * * * *